(12) United States Patent
Rambach

(10) Patent No.: US 9,506,101 B2
(45) Date of Patent: Nov. 29, 2016

(54) **METHOD AND MEDIUM FOR DETECTING SHIGA TOXIN-PRODUCING *ESCHERICHIA COLI* BACTERIA**

(76) Inventor: Alain Rambach, Paris (FR)

( * ) Notice: Subject to any disclaimer, the term of this patent is extended or adjusted under 35 U.S.C. 154(b) by 56 days.

(21) Appl. No.: 13/508,929

(22) PCT Filed: Nov. 10, 2010

(86) PCT No.: PCT/EP2010/067226
§ 371 (c)(1),
(2), (4) Date: Oct. 26, 2012

(87) PCT Pub. No.: WO2011/058065
PCT Pub. Date: May 19, 2011

(65) Prior Publication Data
US 2013/0065264 A1    Mar. 14, 2013

(30) Foreign Application Priority Data
Nov. 10, 2009   (FR) ...................................... 09 05415

(51) Int. Cl.
*C12Q 1/10*    (2006.01)
*C12Q 1/04*    (2006.01)

(52) U.S. Cl.
CPC ................. *C12Q 1/045* (2013.01); *C12Q 1/10* (2013.01)

(58) Field of Classification Search
None
See application file for complete search history.

(56) References Cited

U.S. PATENT DOCUMENTS 7,018,807 B2 *    3/2006   Chen et al. ...................... 435/34
2004/0121404 A1 *    6/2004   Cotte et al. ..................... 435/7.1

FOREIGN PATENT DOCUMENTS

WO     WO 98/11252 A1    3/1998

OTHER PUBLICATIONS

Fukushima, H., et al., "High Numbers of Shiga Toxin-Producing *Escherichia coli* Found in Bovine Faeces Collected at Slaughter in Japan," *FEMS Microbiiology Letters*, 2004, pp. 189-197, vol. 238(1).
Fukushima, H., et al., "Selective Isolation of *eae*-Positive Strains of Shiga Toxin-Producing *Escherichia coli*," *Journal of Clinical Microbiology*, 2000, pp. 1684-1687, vol. 38(4).
Hiramatsu, R., et al., "Characterization of Shiga Toxin-Producing *Escherichia coli* 026 Strains and Establishment of Selective Isolation Media for These Strains," *Journal of Clinical Microbiology*, 2002, pp. 922-925, vol. 40(3).

* cited by examiner

*Primary Examiner* — Suzanne M Noakes
*Assistant Examiner* — Jae W Lee
(74) *Attorney, Agent, or Firm* — Alston & Bird LLP

(57) ABSTRACT

The present invention relates to a method for specific and direct detection of Shiga toxin-producing *Escherichia coli* bacteria in a sample using a selective and differential isolation medium for Shiga toxin-producing *Escherichia coli* bacteria comprising at least one chromogenic agent and tellurite.

2 Claims, No Drawings

METHOD AND MEDIUM FOR DETECTING SHIGA TOXIN-PRODUCING ESCHERICHIA COLI BACTERIA

CROSS-REFERENCE TO RELATED APPLICATIONS

This application is the U.S. National Stage of International Application PCT/EP2010/067226, filed Nov. 10, 2010, which claims the benefit of French Patent Application No. 09 05415, filed Nov. 10, 2009, both of which are hereby incorporated herein in their entirety by reference.

This invention relates to a process for specific and direct detection of Shiga toxin-producing *Escherichia coli* (STEC) bacteria in a sample implementing a selective and differential isolation medium for STEC strains comprising at least one chromogenic agent and tellurite.

The Shiga toxin-producing *E. coli* (STEC) are responsible for foodborne taxi-infection that result in diarrhea as well as more serious syndromes in humans such as hemolytic uremic syndrome, which can provoke death. These are zoonotic agents of which the main reservoir is cattle and other ruminants. The main modes of transmission of STEC infections to humans are consumption of contaminated foods (rare beef, unpasteurized dairy products), transmission from person-to-person, ingestion of contaminated water and contact with animals (in particular cattles) and their environment.

More specifically, the STEC strain of serotype O157:H7 is responsible for epidemics throughout the world. Numerous diagnostic methods have been developed in order to identify this pathogen from foods. These include conventional bacteriology methods, immunological methods and molecular methods. Hygiene measures are particularly important for preventing contamination of farm animals and meat in the slaughterhouse. Finally, risk assessment models have been developed in particular in order to model the behavior of STEC in food.

Although *E. coli* O157 is the most common STEC, other strains are frequently involved in human pathologies. Among these strains, mention may be made of O26, O103, O111 and O145. Few laboratories conduct tests for detecting these non-O157 STECs due to the lack of standardized methods and the cost of the complex equipment necessary for conducting such tests, such as modern PCR methods.

Among the isolation media of the prior art, mention may be made of the sorbitol MacConkey (SMAC) medium, which was developed in order to isolate the negative O157 strains in sorbitol. However, non-O157 strains or positive O157 strains in sorbitol cannot be isolated by using this medium. Modifications of the SMAC medium were proposed and essentially make it possible to increase the selectivity of negative *E. coli* O157 by using inhibitors and/or antibiotics such as CT-SMAC, in which potassium tellurite and cefixime are added to the SMAC medium, and the CR-SMAC medium, in which the cefixime and the rhamnose are added to the SMAC medium in order to improve the efficacy of isolation of O157 strains.

The methods of the prior art using a medium for the isolation of non-O157 STEC strains comprise one or more sugars or alcohols. Such media do not however make it possible to obtain sufficient sensitivity and also lead to false positives, limiting the reliability of the results.

It is therefore important to have tools and processes for detecting these bacteria, which combine both good specificity and selectivity, and in particular ease of use so that it is possible to simplify the tests as much as possible, to conduct them quickly and in large numbers, even automate them, with the objective of ensuring food and/or hospital hygiene, while enabling different STEC strains to be differentiated quickly.

There is therefore a real need to have a simpler, more specific, more direct and less expensive detection technique making it possible to differentiate different STEC strains while avoiding combining a plurality of tests, producing an additional delay in obtaining results and increasing the risk of parasitic contaminations or error as well as the risk of spread of the bacteria.

Surprisingly and unexpectedly, the Inventor has shown that the use of tellurite and a chromogen makes it possible to quickly isolate the STECs in a sensitive and specific manner. In particular, when it is implemented on a solid agar medium, the detection process developed by the Inventor can be carried out directly, for example from a food sample or from a sample collected from a patient, without requiring a preliminary step of isolation of the different strains present in said sample.

In particular, the process according to the invention can be applied to the detection of STEC strains chosen from the group consisting of strains O26, O103, O111, O145 and O157 and even more preferably from the group consisting of strains O26, O103, O111 and O145.

This invention therefore relates to a process for direct detection of Shiga toxin-producing *Escherichia coli* bacteria in a sample comprising the successive steps of;

a) inoculation, with said sample, of a culture medium including tellurite and at least one chromogenic agent, b) incubation of said culture medium under conditions enabling the growth of Shiga toxin-producing *Escherichia coli* bacteria, and c) detection of Shiga toxin-producing *Escherichia coli* bacteria colonies formed on said culture medium.

Advantageously, the process according to the present invention further comprises a step d) making it possible to conclude whether or not a particular strain of bacteria is present according to the color of the colonies formed. This is therefore a step of d) identification of the STEC strain in said sample.

With respect to the previous processes, the process developed by the Inventor enables direct and quick detection of Shiga toxin-producing *Escherichia coli* (STEC) bacteria.

By "biological sample", it is understood any type of microbiological sample, such as, for example, a sample of food material (dairy products, meat, etc.), a soil sample, a sample from a mammal (skin, mucous, etc.), preferably human, or one of its derivatives such as a pre-culture obtained from such a sample.

Advantageously, said biological sample is a liquid biological sample, such as saliva, blood or urine, a solid biological sample, such as feces or a food product, or a derivative of a liquid or solid biological sample such as a pre-culture of such a liquid or solid biological sample.

Also advantageously, said biological sample includes different microorganisms, which may belong to species and even to distinct genera. By way of example, said biological sample includes at least two different microorganisms, preferably at least five different microorganisms, and, particularly preferably, at least ten different microorganisms.

By "culture medium", we mean a medium enabling the growth of said at least one specific microorganism to be detected. Said culture medium indeed includes the nutrients necessary for the growth of said at least one specific microorganism to be detected.

By "nutrients necessary for the growth of said at least one specific microorganism to be detected", we mean the composition of a basic medium necessary for said growth. A person skilled in the art fully knows the composition of such media and is capable of adapting it if necessary according to the specificity of certain microorganisms or constraints that may be associated with certain cases of this invention (transparency of the medium, for example). These nutrients are in particular chosen from the group including carbon, nitrogen, sulphur, phosphorus, vitamins, growth inducers, carbohydrates, salts (for example, calcium, magnesium, manganese, sodium, potassium), nutritional complexes (for example, amino acids, blood, serum, albumin) as well as peptones and animal and plant tissue extracts.

The culture medium used in the context of the present invention for the detection of STEC strains, and which constitutes another subject-matter of this invention, may be in solid, semi-solid, liquid or lyophilized form. Preferably, said culture medium is an agar medium, and is, by way of example, agar-based. Among the presentations of culture media that can be used, mention can thus be made of Petri dishes in which microorganisms are developed.

The culture media according to this invention can optionally contain one or more antimicrobial agents, in particular one or more antibiotics and/or one or more antifungal agents.

Said antimicrobial agent(s) make it possible to limit the growth of microorganisms other than said at least one specific microorganism to be detected.

The effective amount of antimicrobial agent to be used can be determined simply by a person skilled in the art owing to his or her general knowledge.

By "culturing", it is meant inoculating said culture medium with all or some of the biological sample and incubating said inoculated culture medium.

A person skilled in the art will adapt the incubation conditions according to the culture medium, the biological sample and the specific microorganism to be detected according to his general knowledge.

The incubation step can be performed at a temperature of around 30° C. to 43° C., preferably 37° C., for a period of around 18 to 24 hours. However, depending on the means available, a person skilled in the art may adapt the temperature and the duration of this incubation step in view of his general knowledge.

By "direct detection process", it is meant a process that does not include a preliminary step of isolating the different bacterial strains present in the sample, preferably a process that does not comprise a preliminary step of isolating each of the bacterial strains present in the sample.

Indeed, the process according to the invention makes it possible to avoid the step of isolating candidate bacterial colonies which can of then be subjected to a more precise test of confirmation of the STEC property. It therefore applies to a raw sample comprising a mixture of bacteria.

Preferably, the tellurite comprised in said medium is in the form of potassium tellurite.

By "chromogenic agent", it is meant a compound having a precipitating chromophore released after hydrolysis by a specific enzyme. The chromophore thus released gives its color to the colonies including said enzyme.

For example, among the enzymes of which the activity can be used in the context of the present invention, mention may be made in particular of: alpha-galactosidase, beta-D-glucuronidase, beta-D-galactosidase, C8-esterase, beta-glucosidase and beta-glucosaminidase, preferably said enzyme is beta-glucosidase.

Advantageously, the medium according to this invention will comprise at least one chromogenic agent sensitive to the activity of beta-glucosidase and at least one other enzyme chosen from alpha-galactosidase, beta-D-glucuronidase, beta-D-galactosidase, C8-esterase, and beta-glucosaminidase, preferably alpha-galactosidase.

Preferably, the medium according to the present invention will include at least one chromogenic agent sensitive to the activity of beta-glucosidase, and at least one chromogenic agent sensitive to the activity of alpha-galactosidase.

Preferably, the medium according to the present invention will include deoxycholate, and more preferably sodium deoxycholate.

Advantageously, the tellurite concentration in the medium according to the present invention is between 0.5 and 10 mg/L, preferably between 1 and 5 mg/L and even more preferably about 2.5 mg/L.

Advantageously, the concentration of chromogen(s) in the medium according to the present invention is between 10 and 300 mg/L, preferably between 20 and 200 mg/L and even more preferably about 100 mg/L.

The effective amount of tellurite and chromogen(s) in the medium according to the present invention may simply be adjusted by a person skilled in the art in view of his or her general knowledge and the results described in the examples below.

The incubation conditions enabling the growth of STEC strains are well known to a person skilled in the art and are not different from those of traditional methods.

It is possible, for example, to choose, as the culture medium used in the process according to this invention, a CHROMagar™ Orientation medium (CHROMagar, Paris, France), to which tellurite and deoxycholate have been added.

Another objective of the invention relates to the use of a culture medium as described above for the direct detection and differentiation of STEC strains.

The following example is provided by way of illustration and cannot limit the scope of this invention.

EXAMPLE

Direct Detection of Shiga Toxin-Producing *Escherichia Coli* Bacteria by Means of a Medium According to the Present Invention Different samples containing bacteria suspensions are spread directly in a Petri dish including an agar medium including:

peptone and yeast extract 8 g/L;

NaCl 5 gL;

agar 15 g/L;

X-glucoside 0.01 g/L;

Mag-alpha-galactoside 0.01 g/L;

sodium deoxycholate 1 g/L; and tellurite 0.0025 g/L.

After incubation for 18 to 24 hours, the visual analysis of the Petri dishes enables those including STEC strains to be identified directly.

The results are indicated in table 1 below:

TABLE 1

| Strain isolated | Color | Size of colonies in mm |
|---|---|---|
| E. coli O157 H7 | Mauve | 1.5 |
| E. coli O26 | Mauve | 1.5 |
| E. coil O103 | Mauve | Irregular |
| E. coli O111 | Mauve | 1 |
| Klebsiella pneumoniae ND20 | Blue | 2 |
| Proteus AR3919 | Green | 0.5 |
| Enterobacter cloacae ND36* | — | — |
| E. coli AR3740* | — | — |
| Proteus AR5075 | Brown | 0.8 |

*Strains with inhibited growth

Thus, the process according to the invention makes it possible, in a single culture step, to specifically detect and differentiate Shiga toxin-producing *Escherichia coli* bacteria, without the need for a preliminary isolation step or a subsequent differentiation step.

The invention claimed is:

1. A method for direct detection of Shiga toxin-producing *Escherichia coli* bacteria chosen from the group consisting of O26, O103, O111 and O145 strains in a sample comprising the successive steps of:
   a) inoculation, with said sample, of a culture medium comprising tellurite and at least one chromogenic agent sensitive to the activity of beta-glucosidase, wherein said culture medium does not contain sorbitol,
   b) incubation of said culture medium under conditions enabling the growth of Shiga toxin-producing *Escherichia coli* bacteria chosen from the group consisting of O26, O103, O111 and O145 strains, and
   c) detection of colonies formed on said culture medium corresponding to Shiga toxin-producing *Escherichia coli* bacteria chosen from the group consisting of O26, O103, O111 and O145 strains.

2. The method of claim 1, wherein said method does not comprise a preliminary step of isolating the different bacterial strains present in the sample.

* * * * *